US005605680A

United States Patent [19]
Deflandre et al.

[11] Patent Number: 5,605,680
[45] Date of Patent: Feb. 25, 1997

[54] PHOTOSTABLE COSMETIC COMPOSITION CONTAINING A UV-A SCREEN AND A UV-B SCREEN AND A PROCESS FOR STABILIZING THE UV-A SCREEN WITH THE UV-B SCREEN

[75] Inventors: Andre Deflandre, Orry-la-Ville; Serge Forestier, Claye-Souilly; Gerard Lang, Saint-Gratien; Jean F. Grollier, Paris; Jean Cotteret, Verneuil-sur-Seine, all of France

[73] Assignee: L'Oreal, Paris, France

[21] Appl. No.: 487,484

[22] Filed: Jun. 7, 1995

Related U.S. Application Data

[63] Continuation of Ser. No. 51,282, Apr. 23, 1993, which is a continuation of Ser. No. 857,105, Mar. 24, 1992, abandoned, which is a continuation of Ser. No. 129,048, Dec. 7, 1987, abandoned.

[30] Foreign Application Priority Data

Dec. 8, 1986 [LU] Luxembourg ............................. 86703

[51] Int. Cl.$^6$ ............................................. A61K 7/42
[52] U.S. Cl. ........................... 424/59; 514/685; 568/304
[58] Field of Search ............................. 424/59; 514/685

[56] References Cited

FOREIGN PATENT DOCUMENTS

| 2440933 | 11/1979 | France . |
| 2513992 | 10/1981 | France . |
| 2574660 | 12/1985 | France . |
| 2038807 | 11/1979 | United Kingdom . |
| 2081716 | 8/1981 | United Kingdom . |
| 2121801 | 6/1983 | United Kingdom . |
| 2157174 | 4/1985 | United Kingdom . |
| 2170105 | 1/1986 | United Kingdom . |

OTHER PUBLICATIONS

Checchi et al, Chem. Abs., 1987, vol. 106, 201530d.
Lang et al, Chem. Abs., 1987, vol. 106, 38240y.
Cosmetic Toiletries, 1986. vol. 101, p. 155.

Primary Examiner—Shelley A. Dodson
Attorney, Agent, or Firm—Jacobson, Price, Holman & Stern, PLLC

[57] ABSTRACT

The invention relates to a photostable screening cosmetic composition for protecting human skin against UV rays, comprising, in a cosmetically acceptable substrate containing at least one fatty phase, 1 to 3% by weight of 4-(1,1-dimethylethyl)-4'-methoxydibenzoylmethane and at least 4.5% by weight of p-methylbenzylidenecamphor, the weight ratio of p-methylbenzylidenecamphor to 4-(1,1-dimethylethyl)-4'-methoxydibenzoylmethane being higher than or equal to 3.

It also relates to a process for protecting the skin against UV radiation and to a process for stabilizing 4-(1,1-dimethylethyl)-4'-methoxydibenzoylmethane against UV radiation.

14 Claims, No Drawings

PHOTOSTABLE COSMETIC COMPOSITION CONTAINING A UV-A SCREEN AND A UV-B SCREEN AND A PROCESS FOR STABILIZING THE UV-A SCREEN WITH THE UV-B SCREEN

This is a continuation of application Ser. No. 08/051,282, filed Apr. 23, 1993, which is a continuation of application Ser. No. 07/857,105, filed Mar. 24, 1992, abandoned, which is a continuation of application Ser. No. 07/129,048, filed Dec. 7, 1987, abandoned.

The present invention relates to a photostable cosmetic composition intended to protect the skin against UV radiation, containing, in combination, a UV-A screen and a UV-B screen which are quite special and to its use for protecting the skin against the UV rays, and to a process for stabilizing the UV-A screen by means of the UV-B screen.

It is known that light radiations of wavelengths between 280 nm and 400 nm permit the human skin to tan and that rays of wavelengths between 280 and 320 nm, known by the name of UV-B, cause erythemas and skin burns which can be detrimental to the development of tanning; this UV-B radiation must therefore be filtered out.

It is also known that the UV-A rays, of wavelengths between 320 and 400 nm, causing tanning of the skin, are capable of giving rise to impairment of the latter, especially in the case of a sensitive skin or of a skin which is continually exposed to solar radiation. In particular, the UV-A rays cause a loss of skin elasticity and the appearance of wrinkles leading to premature aging. They promote the onset of the erythemateous reaction or intensify this reaction in some individuals and may be at the origin of phototoxic or photoallergic reactions. It is therefore also desirable to filter out the UV-A radiation.

French Patent No. 2,440,933 describes, as a UV-A screen, 4-(1,1-dimethylethyl)-4'-methoxydibenzoylmethane whose absorption maximum is situated at 355 nm. This UV-A screen is sold under the name "Parsol 1789" by Givaudan. In this patent it is proposed to combine this UV-A screen with various UV-B screens with the aim of absorbing all the UV radiation of wavelengths between 280 and 380 nm. The preferred UV-B screen for employment in combination with 4-(1,1-dimethylethyl)-4'-methoxydibenzoylmethane is 2-ethylhexyl p-methoxycinnamate sold under the name "Parsol MCX" by Givaudan.

Unfortunately, in this combination, 4-(1,1-di-methylethyl)-4'-methoxydibenzoylmethane does not have a sufficient photochemical stability to guarantee a continuous protection during a prolonged exposure to the sun, and this means that frequent and repeated applications at regular intervals are necessary when it is desired to obtain an effective protection of the skin against the UV rays.

The Applicant has found that by combining 4-(1,1-dimethylethyl)-4'-methoxydibenzoylmethane with p-methylbenzylidenecamphor sold under the name "Eusolex 6300" by Merck, in proportions and in a weight ratio which are well defined, a remarkable photochemical stability of 4-(1,1-dimethylethyl)-4'-methoxydibenzoylmethane was obtained, in a surprising manner.

As a result of their liposoluble nature, they are distributed uniformly in conventional cosmetic substrates containing at least one fatty phase and may thus be applied to the skin to form an effective protective film.

The subject of the present invention is therefore a photostable cosmetic composition protecting the skin against the UV radiation, comprising in a cosmetically acceptable substrate containing at least one fatty phase, 1 to 3% by weight of 4-(1,1-dimethylethyl)-4'-methoxydibenzoylmethane and at least 4.5% by weight of p-methylbenzylidenecamphor, the weight ratio of p-methylbenzylidenecamphor to 4-(1,1-dimethylethyl)-4'-methoxydibenzoylmethane being higher than or equal to 3.

For reasons of solubilization of the screens in the composition, this ratio is preferably lower than or equal to 6, but is not critical.

Another subject of the present invention is a process for protecting the skin against solar radiation consisting in applying to the skin an effective quantity of a cosmetic composition such as defined hereinbefore.

Another subject of the invention consists in a process for stabilizing 4-(1,1-dimethylethyl)-4'-methoxydibenzoylmethane against UV radiation with the aid of p-methylbenzylidenecamphor, in which process at least 4.5% by weight of p-methylbenzylidenecamphor are employed to stabilize 1 to 3% by weight of 4-(1,1-dimethylethyl)-4'-methoxydibenzoylmethane, the weight ratio of p-methylbenzylidenecamphor to 4-(1,1-dimethylethyl)-4'-methoxydibenzoylmethane being higher than or equal to 3.

Because of the liposoluble nature of the two screens employed, the cosmetic compositions according to the invention contain at least one fatty phase. They may be in the form of oily or oleoalcoholic lotions, in the form of fatty or oleoalcoholic gels, of solid sticks or else in the form of emulsions such as a cream or a milk; they may be packaged as an aerosol.

As solubilizing solvent, there may be employed an oil or a wax, a lower monoalcohol or a lower polyol or mixtures thereof. Monoalcohols or polyols which are particularly preferred are ethanol, isopropanol, propylene glycol and glycerine.

The cosmetic composition according to the invention which is intended to protect human skin against the ultraviolet rays may contain the cosmetic adjuvants which are commonly used in a composition of this type, such as thickeners, softeners, humectants, surfactants, preservatives antifoams, oils, waxes, lanolin, perfumes, propellants, colorants and/or pigments whose function is to colour the composition itself or the skin, or any other ingredient usually employed in cosmetics.

An embodiment of the invention is an emulsion in the form of a cream or milk comprising, in addition to the combination of the two UV-A and UV-B screens, fatty alcohols, fatty acid esters and especially fatty acid triglycerides, fatty acids, lanolin, natural or synthetic oils and emulsifiers, in the presence of water.

Another embodiment consists of oily lotions based on fatty acid esters, on natural or synthetic oils and/or waxes or on oleoalcoholic lotions based on oils or waxes, fatty acid esters such as fatty acid triglycerides and lower alcohols such as ethanol or glycols such as propylene glycol and/or polyols such as glycerine.

The oleoalcoholic gels comprise an oil or a wax, a lower alcohol or polyol such as ethanol, propylene glycol or glycerine and a thickener such as silica.

The solid sticks consist of natural or synthetic waxes and oils, fatty alcohols, fatty acid esters, lanolin and fatty substances.

In the case of a composition which is packaged as an aerosol, conventional propellants such as alkanes, fluoroalkanes and chlorofluoroalkanes are employed.

The following examples are intended to illustrate the invention without, however, being of a limiting nature.

EXAMPLE 1

Water-in-oil emulsion

| | |
|---|---|
| 4-(1,1-Dimethylethyl)-4'-methoxydibenzoylmethane (Parsol 1789) | 1.5 g |
| p-Methylbenzylidenecamphor (Eusolex 6300) | 4.5 g |
| Mixture of cetylstearyl alcohol and of cetyl-stearyl alcohol oxyethylenated with 33 moles of ethylene oxide | 7.3 g |
| Mixture of glycerol mono- and distearate | 2.1 g |
| Triglycerides of $C_8$–$C_{12}$ fatty acids | 31.4 g |
| Polydimethylsiloxane | 1.6 g |
| Cetyl alcohol | 1.6 g |
| Water q.s. | 100 g |

This emulsion is prepared according to conventional methods by dissolving the screens in the fatty phase containing the emulsifiers, heating this fatty phase to about 80°–85° C. and vigorous stirring, water which has been preheated to around 80° C.

To evaluate the stability of "Parsol 1789", the emulsion is spread in the form of a film with a thickness of 10 μm between two quartz plates. The quantity deposited is determined by weighing. The films are irradiated with the aid of a solar simulator.

After irradiation, the two quartz plates are separated and immersed in 5 ml of isopropanol. The whole is stirred for 30 minutes, and then the solution is filtered through a 0.45 μm porosity Millipore filter. The content of the UV-A "Parsol 1789" screen is then determined by high-performance liquid phase chromatography.

It is found that after one hour's irradiation, the loss of "Parsol 1789" in the emulsion containing the "Parsol 1789 - Eusolex 6300" combination is very low compared with the loss of "Parsol 1789" when the latter is combined with "Parsol MCX", that is to say 2-ethylhexyl p-methoxycinnamate.

EXAMPLE 2

Oily lotion

The following ingredients are mixed, with optional heating to 40°–45° C. in order to homogenize:

| | |
|---|---|
| 4-(1,1-Dimethylethyl)-4'-methoxydibenzoylmethane (Parsol 1789) | 1.5 g |
| p-Methylbenzylidenecamphor (Eusolex 6300) | 4.5 g |
| Isopropyl myristate q.s. | 100 g |

When the test described in Example 1 is carried out, it is found that the loss of "Parsol 1789" in the presence of "Eusolex 6300" after one hour's irradiation is low when compared with the loss of "Parsol 1789" measured under the same conditions but in the presence of 2-ethylhexyl p-methoxycinnamate.

EXAMPLE 3

Oily lotion

Using the same procedure as in Example 2, an oily lotion is prepared from the following ingredients:

| | |
|---|---|
| 4-(1,1-Dimethylethyl)-4'-methoxydibenzoylmethane (Parsol 1789) | 1 g |
| p-Methylbenzylidenecamphor (Eusolex 6300) | 5 g |
| Miglyol 812 (triglycerides of $C_8$–$C_{12}$ fatty acids) q.s. | 100 g |

EXAMPLE 4

Oily lotion

The following oily lotion is prepared:

| | |
|---|---|
| 4-(1,1-Dimethylethyl)-4'-methoxydibenzoylmethane (Parsol 1789) | 2 g |
| p-Methylbenzylidenecamphor (Eusolex 6300) | 8 g |
| Miglyol 812 q.s. | 100 g |

When the test described in Example 1 is carried out, it is found that the loss of "Parsol 1789" in the lotions of Examples 3 and 4, after one hour's irradiation, is low when compared with that measured in the absence of "Eusolex 6300".

We claim:

1. A sunscreening cosmetic composition wherein 4-(1,1-dimethylethyl)-4'-methoxydibenzoylmethane is stabilized against UV radiation, consisting essentially of at least 4.5% by weight of p-methylbenzylidenecamphor, 1 to 3% by weight of 4-(1,1-dimethylethyl)-4'-methoxydibenzoylmethane, the weight ratio of p-methylbenzylidenecamphor to 4-(1,1-dimethylethyl)-4'-methoxydibenzoylmethane being higher than or equal to 3, and a cosmetically acceptable substrate containing at least one fatty phase, said substrate being in a form selected from the group consisting of oily and oleoalcoholic lotions, fatty and oleoalcoholic gels, solid sticks, emulsions and aerosols, said substrate containing at least one cosmetic adjuvant selected from the group consisting of thickeners, softeners, humectants, surfactants, preservatives, antifoaming agents, perfumes, oils, waxes, lower monoalcohols, lower polyols, propellants, colorants and pigments.

2. A composition according to claim 1, wherein the weight ratio of p-methylbenzylidenecamphor to 4-(1,1-dimethylethyl)-4'-methoxydibenzoylmethane is lower than or equal to 6.

3. A composition according to claim 1, wherein said substrate is in the form of an aqueous emulsion selected from the group consisting of a cream and a milk additionally comprising a member selected from the group consisting of fatty alcohols, fatty acid esters, fatty acids, lanolin, natural and synthetic oils and waxes and emulsifiers.

4. A composition according to claim 1, wherein said substrate is in the form of an oily lotion additionally comprising a member selected from the group consisting of fatty acid esters, and natural and synthetic oils and waxes.

5. A composition according to claim 1, wherein said substrate is in the form of an oleoalcoholic lotion additionally comprising a member selected from the group consisting of oils, waxes, fatty acid esters and lower alcohols, glycols and polyols.

6. A composition according to claim 1, wherein said substrate is in the form of an oleoalcoholic gel additionally comprising a member selected from the group consisting of natural and synthetic oils and waxes, lower alcohols, lower polyols and thickeners.

7. In an improved composition for protecting human skin against UV radiation comprising a sunscreening cosmetic composition containing 4-(1,1-dimethylethyl)-4'-methoxydibenzoylmethane as a UV-A sunscreen in combination with a UV-B sunscreen in a cosmetically acceptable substrate, wherein the improvement consists essentially of using at least 4.5% by weight of p-methylbenzylidenecamphor as the UV-B sunscreen and 1 to 3% by weight of 4-(1,1-dimethylethyl)-4'-methoxydibenzoylmethane as the UV-A sunscreen, the weight ratio of p-methylbenzylidenecamphor to 4-(1,1-dimethylethyl)-4'-methoxydibenzoylmethane being higher than or equal to 3, said substrate containing at least one fatty phase, said substrate being in a form selected from the group consisting of oily and oleoalcoholic lotions, fatty and oleoalcoholic gels, solid sticks, emulsions and aerosols, said substrate containing at least one cosmetic adjuvant selected from the group consisting of thickeners, softeners, humectants, surfactants, preservatives, antifoaming agents, perfumes, oils, waxes, lower monoalcohols, lower polyols, propellants, colorants and pigments, whereby 4-(1,1-dimethylethyl)-4'-methoxydibenzoylmethane is stabilized against UV radiation.

8. A process for stabilizing 4-(1,1-dimethylethyl)-4'-methoxydibenzoylmethane against UV radiation, consisting essentially of adding at least 4.5% by weight of p-methylbenzylidenecamphor to a sunscreening cosmetic composition consisting essentially of 1 to 3% by weight of 4-(1,1-dimethylethyl)-4'-methoxydibenzoylmethane and a cosmetically acceptable substrate, the weight ratio of p-methylbenzylidenecamphor to 4-(1,1-dimethylethyl)-4'-methoxydibenzoylmethane being higher than or equal to 3, said substrate containing at least one fatty phase, said substrate being in a form selected from the group consisting of oily and oleoalcoholic lotions, fatty and oleoalcoholic gels, solid sticks, emulsions and aerosols, said substrate containing at least one cosmetic adjuvant selected from the group consisting of thickeners, softeners, humectants, surfactants, preservatives, antifoaming agents, perfumes, oils, waxes, lower monoalcohols, lower polyols, propellants, colorants and pigments.

9. A process according to claim 8, wherein the weight ratio of p-methylbenzylidenecamphor to 4-(1,1-dimethylethyl)-4'-methoxydibenzoylmethane is lower than or equal to 6.

10. A process according to claim 8, wherein said substrate is in the form of an aqueous emulsion selected from the group consisting of a cream and a milk additionally comprising a member selected from the group consisting of fatty alcohols, fatty acid esters, fatty acids, lanolin, natural and synthetic oils and waxes and emulsifiers.

11. A process according to claim 8, wherein said substrate is in the form of an oily lotion additionally comprising a member selected from the group consisting of fatty acid esters, and natural and synthetic oils and waxes.

12. A process according to claim 8, wherein said substrate is in the form of an oleoalcoholic lotion additionally comprising a member selected from the group consisting of oils, waxes, fatty acid esters and lower alcohols, glycols and polyols.

13. A process according to claim 8, wherein said substrate is in the form of an oleoalcoholic gel additionally comprising a member selected from the group consisting of natural and synthetic oils and waxes, lower alcohols, lower polyols and thickeners.

14. In an improved process for protecting human skin against UV radiation comprising applying to the skin an effective amount of a sunscreening cosmetic composition containing 4-(1,1-dimethylethyl)-4'-methoxydibenzoylmethane as a UV-A sunscreen in combination with a UV-B sunscreen in a cosmetically acceptable substrate, wherein the improvement consists essentially of using at least 4.5% by weight of p-methylbenzylidenecamphor as the UV-B sunscreen and 1 to 3% by weight of 4-(1,1-dimethylethyl)-4'-methoxydibenzoylmethane as the UV-A sunscreen, the weight ratio of p-methylbenzylidenecamphor to 4-(1,1-dimethylethyl)-4'-methoxydibenzoylmethane being higher than or equal to 3, said substrate containing at least one fatty phase, said substrate being in a form selected from the group consisting of oily and oleoalcoholic lotions, fatty and oleoalcoholic gels, solid sticks, emulsions and aerosols, said substrate containing at least one cosmetic adjuvant selected from the group consisting of thickeners, softeners, humectants, surfactants, preservatives, antifoaming agents, perfumes, oils, waxes, lower monoalcohols, lower polyols, propellants, colorants and pigments, whereby 4-(1,1-dimethylethyl)-4'-methoxydibenzoylmethane is stabilized against UV radiation.

\* \* \* \* \*